United States Patent
Kleiner

Patent Number: 5,869,722
Date of Patent: Feb. 9, 1999

[54] PROCESS FOR PRODUCING ALUMINUM PHOSPHINATES

[75] Inventor: Hans-Jerg Kleiner, Kronberg, Germany

[73] Assignee: Ticona GmbH, Germany

[21] Appl. No.: 844,749

[22] Filed: Apr. 22, 1997

[30] Foreign Application Priority Data

Apr. 23, 1996 [DE] Germany ............... 196 16 025.1

[51] Int. Cl.$^6$ ................................. C07F 9/02
[52] U.S. Cl. .................................... 556/174
[58] Field of Search ............................. 556/174

[56] References Cited

FOREIGN PATENT DOCUMENTS

| 0 699 708 | 3/1996 | European Pat. Off. |
| 4430932 | 3/1996 | Germany . |

OTHER PUBLICATIONS

Poly [tris (dialkylphosphinato)alanes]. Novel Tris(phosphinates) of Aluminum. Edward E. Flagg; Donald L. Schmidt *J. Amer. Chem. Soc.* 90(15) pp. 4173–4174, 1968.

Inorg. Macromol. Rev. 1, 115 (1970) Polymeric Metal Phosphinates B. P. Block, 1970.

Transition Met. Chem. (Weinheim, Ger.) (TMCHDN, 03404285); 81;vol. 6 (2); pp. 79–82, Beaver Coll.; Dep. Phys.; Glenside; 19038; PA; USA, XP000675826 Mikulski C. Metal "Methylphenylphosphinate complexes with tri– and tetra–positive metal ions".

J. Polym. Sci., Part A–1 (JPLCAT); 70; vol. 8 (1); pp. 1–14, Dow Chem. Co.; Midland; Mich., XP000676830 Flagg et al; "Poly[tris(diorganopholsphinato)alanes]".

Z. Naturforsch., B: Chem. Sci. (NNBSEN, 0–9320776); 91; vol. 46 (11); pp. 1568–1570, Univ. United Arab Emirates; Coll. Sci.; United Arab Emirates (AE), XP000674673 Shihada et al: "Preparation and vibrational spectra of Me2Sn (02PM32)2, CL2Sn(02PM2)2, and A1(02PM32)3".

Mikulski, C. M., et al, *Transition Met. Chem.* 6:79–82 (1981).

*Primary Examiner*—Porfirio Nazario-Gonzalez
*Assistant Examiner*—Brian J. Davis
*Attorney, Agent, or Firm*—Connolly & Hutz

[57] ABSTRACT

Process for producing aluminum phosphinates

The invention relates to a process for producing aluminum phosphinates of the formula (I)

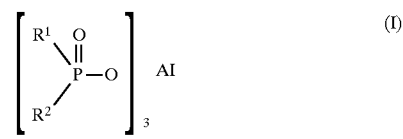

where $R^1$ and $R^2$, independently of each other, are linear or branched ($C_1$–$C_6$)-alkyl or phenyl, which comprises reacting phosphinates of the formula (II)

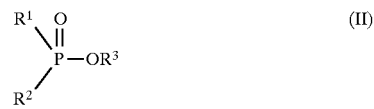

where $R^1$ and $R^2$ are as previously stated and $R^3$ is $C_1$–$C_6$-alkyl, with aluminum chloride in a molar ratio of from 2.5:1 to 4:1.

15 Claims, No Drawings

PROCESS FOR PRODUCING ALUMINUM PHOSPHINATES

DESCRIPTION

Process for producing aluminum phosphinates

The invention relates to a process for producing aluminum phosphinates.

Aluminum salts of phosphinic acids are known as valuable flame retardants. They are prepared from the corresponding phosphinic acids using aluminum hydroxide in water at about 80°–100° C. For example, ethylmethylphosphinic acid and aluminum hydroxide give the desired salt in 95% yield after a total reaction time of 65 hours (German Offenlegungsschrift 44 30 932). The disadvantage of this industrially interesting process is the long reaction time. Preparation starting from the phosphinic acids is furthermore disadvantageous in that the phosphinic acids must be prepared from the corresponding phosphinic acid esters by hydrolysis at high temperatures. In addition to this, a process is known for preparing poly(metal phosphinates) in which esters of methylphenylphosphinic acid are reacted with aluminum chloride to give poly(aluminum phosphinates). The yields in this process are almost quantitative (C. M. Mikulski et al., Transition Met. Chem. 6, 79 (1981)). The disadvantage of this process is that the phosphinic acid esters must be employed in large excess, with the reaction temperature held at between 50°–200° C. The excess is about from 4 to 5 times the theoretical amount (15 to 20 cm$^3$ per gram of aluminum chloride).

There is therefore a need for a simplified process which allows the aluminium phosphinates to be obtained in a simple manner directly from phosphinic acid esters.

This object was, surprisingly, achieved by a process for producing aluminum phosphinates of the formula (I)

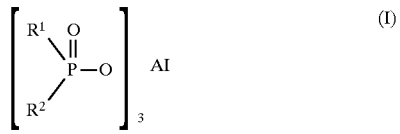

where $R^1$ and $R^2$, independently of each other, are linear or branched $(C_1-C_6)$-alkyl or phenyl, which comprises reacting phosphinates of the formula (II)

where $R^1$ and $R^2$ are as previously stated and $R^3$ is $C_1-C_6$-alkyl, with aluminum chloride in a molar ratio of 2.5:1 to 4:1.

Of importance is the reaction of compounds of the formula (II) where $R^1$, $R^2$ and $R^3$ are $(C_1-C_4)$-alkyl, in particular methyl, ethyl, n-propyl or isobutyl.

Of particular interest is the reaction of methyl dimethylphosphinate, ethyl ethylmethylphosphinate, butyl ethylmethylphosphinate, amyl ethylmethylphosphinate, n-butyl ethylpropylphosphinate, n-butyl propylmethylphosphinate, n-butyl isobutylmethylphosphinate, n-butyl hexylmethylphosphinate, and methyl diphenylphosphinate.

In the process, aluminum chloride is metered into the ester, with cooling if desired, in a molar ratio of from 2.5:1 to 4:1. Surprisingly, the aluminum chloride dissolves. It is advantageous to employ the phosphinate and aluminum chloride in a molar ratio of from 2.8:1 to 3.5:1, in particular 3:1. After the dissolution process is complete, the temperature is raised, the reaction begins and the aluminum salt of the phosphinic acid precipitates. The reaction can be highly exothermic, in particular if $R^3=C_1-C_3$-alkyl, in which case cooling may be necessary after the reaction temperature has been reached. It may also be expedient to introduce the aluminum chloride in batches at the reaction temperature, with simultaneous formation of the end product, which makes the process easier to design from the safety point of view.

Reaction temperatures in the range from 40° to 120° C., in particular from 50° to 80° C., have proved successful. It may also be expedient to add inert solvents, in particular isobutyl chloride, pentyl chloride, toluene or xylene. At the end of the reaction, when chloride ions detectable in only tiny amounts, alcohols or acetone, ethyl methyl ketone or acetonitrile can be employed as diluents. As a result of the method of preparation, the salts obtained are almost water-free and therefore do not need complex drying measures. They can be employed directly without further purification operations.

EXAMPLE 1

26.7 g (0.2 mol) of aluminum chloride are introduced in portions with cooling into 81.6 g (0.6 mol) of ethyl ethylmethylphosphinate, the temperature climbing to 70° C. as a result of the exothermic reaction. At the same time, ethyl chloride gas is evolved, which remains in a cold trap attached downstream of the apparatus. When all the aluminum chloride has been introduced, the mixture is slowly heated to 100° C. and held at that temperature until no further gas evolution is detected. The reaction mixture now comprises about 69 g of aluminum ethylmethylphosphinate having a water content of 200 ppm. The melting point is above 360° C. The yield is almost 100% of theoretical.

EXAMPLE 2

26.7 g (0.2 mol) of aluminum chloride are introduced in portions, with cooling and stirring, into 98.4 g (0.6 mol) of n-butyl ethylmethylphosphinate, during which the aluminum chloride dissolves. The mixture is then heated to from 70° to 80° C. and reflux begins. The aluminum ethylmethylphosphinate begins to precipitate. 100 ml of isobutyl chloride are added as diluent during the reaction, which proceeds at about 70° C. After refluxing for 12 hours, the mixture is cooled and filtered with suction, and the filter cake is washed with isobutyl chloride. Brief drying at 100° C. in a vacuum drying cabinet gives 63 g of aluminum ethylmethylphosphinate having a water content of 200 ppm. The melting point is above 360° C. The yield is 91% of theoretical.

I claim:

1. A process for producing an aluminum phosphinate of the formula (I)

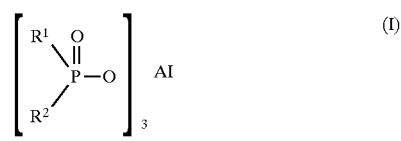

where $R^1$ and $R^2$, independently of each other, are linear or branched $(C_1-C_6)$-alkyl or phenyl, which comprises reacting phosphinate of the formula (II)

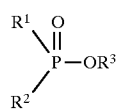

where $R^1$ and $R^2$ are as previously stated and $R^3$ is $C_1$–$C_6$-alkyl, with aluminum chloride in a phosphinate:aluminum chloride molar ratio of from 2.5:1 to 4:1.

2. The process as claimed in claim 1, wherein the compound of formula (II) is methyl dimethylphosphinate, ethyl ethylmethylphosphinate, butyl ethylmethylphosphinate, amyl ethylmethylphosphinate, n-butyl ethylpropylphosphinate, n-butyl propylmethylphosphinate, n-butyl isobutylmethylphosphinate, n-butyl hexylmethylphosphinate or methyl diphenylphosphinate.

3. The process as claimed in claim 1, wherein the phosphinate of formula (II) is the initial charge to a reaction zone, the aluminum chloride is metered in to the reaction zone and then the temperature is raised to from 40° to 120° C.

4. The process as claimed in claim 1, wherein an inert solvent is added as a diluent during the reaction between the phosphinate of formula(II) and the aluminum chloride.

5. The process as claimed in claim 1, wherein the phosphinate:aluminum chloride molar ratio is from 2.8:1 to 3.5:1.

6. The process as claimed in claim 1, wherein $R^1$, $R^2$ and $R^3$ are ($C_1$–$C_4$)-alkyl.

7. The process as claimed in claim 6, wherein $R^1$, $R^2$ and $R^3$ are methyl, ethyl, n-propyl or isobutyl.

8. The process as claimed in claim 1, wherein aluminum chloride is added in a portionwise manner to a phosphinate of formula (II).

9. The process as claimed in claim 3, wherein said temperature is raised from 50° to 80° C.

10. The process as claimed in claim 1, wherein the aluminum chloride is added to a phosphinate of formula (II) in portions, with cooling of the resulting reaction mixture; the temperature of the reaction mixture is then allowed to increase as a result of a reaction exotherm, and further heating of the reaction mixture is not begun until all the aluminum chloride has been added.

11. The process as claimed in claim 1, wherein the resulting aluminum phosphinate of formula (I) is recovered as a precipitate from the resulting reaction mixture.

12. The process as claimed in claim 4, wherein said inert solvent is isobutyl chloride, pentyl chloride, toluene, or xylene.

13. The process as claimed in claim 8, wherein the phosphinate:aluminum chloride molar ratio ranges from 2.8:1 to 3.5:1.

14. The process as claimed in claim 5, wherein said phosphinate:aluminum chloride molar ratio is 3:1.

15. The process as claimed in claim 8, wherein the aluminum chloride is reacted with the phosphinate of formula (II) in batches at the reaction temperature.

* * * * *